United States Patent [19]
Berg

[11] Patent Number: 6,024,841
[45] Date of Patent: Feb. 15, 2000

[54] SEPARATION OF 2-METHYL-1-BUTANOL AND 3-METHYL-1-BUTANOL FROM 1-PENTANOL BY EXTRACTIVE DISTILLATION

[76] Inventor: Lloyd Berg, 1314 S. 3rd Ave., Bozeman, Mont. 59715

[21] Appl. No.: 09/292,782

[22] Filed: Apr. 13, 1999

[51] Int. Cl.⁷ .............................. B01D 3/40; C07C 29/84
[52] U.S. Cl. .................. 203/57; 203/58; 203/59; 203/60; 203/62; 203/63; 203/64; 203/65; 203/68; 203/69; 203/70; 568/913
[58] Field of Search .................. 203/60, 57, 62, 203/63, 64, 65, 69, 58, 70, 68, 59; 568/913

[56] References Cited

U.S. PATENT DOCUMENTS

| | | | |
|---|---|---|---|
| 4,428,798 | 1/1984 | Zudkeritch et al. | 203/65 |
| 4,482,768 | 11/1984 | Somekh | 568/913 |
| 5,160,414 | 11/1992 | Lee et al. | 568/913 |
| 5,407,541 | 4/1995 | Berg | 203/68 |
| 5,417,814 | 5/1995 | Berg | 203/60 |
| 5,763,695 | 6/1998 | Beg | 203/57 |
| 5,779,862 | 7/1998 | Berg | 203/59 |
| 5,789,629 | 8/1998 | Berg | 203/62 |

*Primary Examiner*—Virginia Manoharan

[57] ABSTRACT

2-Methyl-1-butanol and 3-methyl-1-butanol are difficult to separate from 1 pentanol by conventional distillation or rectification because of the proximity of their boiling points. 2-Methyl-1-butanol and 3-methyl-1-butanol can be easily separated from 1-pentanol by extractive distillation. Effective agents are 3-carene, propylene glycol phenyl ether and dimethylsulfoxide.

1 Claim, No Drawings

SEPARATION OF 2-METHYL-1-BUTANOL AND 3-METHYL-1-BUTANOL FROM 1-PENTANOL BY EXTRACTIVE DISTILLATION

FIELD OF THE INVENTION

This invention relates to a method for separating 2-methyl-1-butanol and 3-methyl-1-butanol from 1-pentanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celsius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

TABLE 1

Effect of Relative Volatility on Theoretical stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 2 | 7 |
| 0.98 | 392 | 81 | 42 | 21 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Methyl-1-butanol and 3-methyl-1-butanol both boil at 130° C. and cannot be separated from each other by distillation. 1-Pentanol boils at 136° C., only six degrees apart and the relative volatility between 1-pentanol and the two methyl butanols is 1.14, making it impossible to separate 1-pentanol from the methyl butanols by conventional rectification. Table 2 shows that with an agent giving a relative volatility of 1.55, only 28 actual plates are required to get 99% purity.

TABLE 2

Theoretical and Actual Plates Required vs. Relative Volatility for 2-Methyl 1-butanol and 3-Methyl-1-butanol from 1-Pentanol Separation

| Relative Volatility | Theoretical Plates Required At Total Reflux, 99% Purity | Actual Plates Required, 75% Eff. |
|---|---|---|
| 1.28 | 38 | 51 |
| 1.45 | 25 | 34 |
| 1.55 | 21 | 28 |

OBJECTIVE OF THE INVENTION

The object of this invention is to provide a process or method of extractive distillation that will enhance the relative volatility of 2-methyl-1-butanol and 3-methyl-1-butanol from 1-pentanol in their separation in a rectification column. It is a further object of this invention to identify effective azeotropic distillation agents that are stable and can be recycled. SUMMARY OF THE INVENTION The objects of the this invention are provided by a process for the separation 2-methyl-1-butanol and 3-methyl-1-butanol from 1-pentanol which entails the use of certain organic compounds when employed as the agent in extractive distillation.

TABLE 3

Effective Extractive Distillation Agents For Separating 2-Methyl-1-butanol And 3 Methyl-1-butanol From 1-Pentanol

| Compounds | Relative Volatility |
|---|---|
| None | 1.14 |
| Ethyl benzoate | 1.43 |
| Ethyl valerate | 1.4 |
| 2-Octanone | 1.45 |
| 2,6-Dimethyl-4-heptanone | 1.5 |
| 2-Undecanone | 1.43 |
| Propiophenone | 1.45 |
| 3-Methoxyacetophenone | 1.42 |
| Propylene glycol phenyl ether | 1.5 |
| 2-Dimethylamino-2-methyl-1-propanol | 1.43 |
| Nitrobenzene | 1.42 |
| 2-Nitrotoluene | 1.4 |
| 3-Nitrotoluene | 1.4 |
| 1-Methylpiperazine | 1.43 |
| Butyrolactone | 1.4 |
| Phenol | 1.44 |
| 2,6-Dimethyl phenol | 1.4 |
| N,N-Dimethylformamide | 1.4 |
| Diethylene glycol methyl ether | 1.4 |
| 1-Octene | 1.5 |
| 1,2,3,4-Tetrahydronaphthalene | 1.42 |
| Dipentene | 1.5 |
| 3-Carene | 1.45 |
| alpha-Pinene | 1.4 |
| Dimethylsulfoxide | 1.6 |
| Tetraethyl ortho silicate | 1.4 |
| N,N-Dimethyl aniline | 1.4 |
| Cyclohexyl amine | 1.45 |

DETAILED DESCRIPTION OF THE INVENTION

I have discovered that certain organic compounds will effectively increase the relative volatility between 2-methyl-1-butanol and 3-methyl-1-butanol from 1-pentanol during rectification when employed as the agent in extractive distillation. They are ethyl benzoate, ethyl valerate, 2-octanone, 2, 6-dimethyl-4-heptanone, 2-undecanone, propiophenone, 3-methoxyacetophenone, propylene glycol phenyl ether, 2-dimethylamino-2-methyl-1-propanol, nitrobenzene, 2-nitrotoluene, 3-nitrotoluene, 1-methylpiperazlie, butyrolactone, phenol, 1-octene, 2,6-dimethyl phenol, N,N-dimethylformamide, diethylene glycol methyl ether, 1,2,3,4-tetrabydronapthalene, dipentene, 3-carene, alpha-pinene, dimethylsulfoxide, tetraethyl ortho silicate, N,N-dimethyl aniline and cyclohexyl amine

THE USEFULNESS OF THE INVENTION

The usefulness or utility of this invention can be demonstrated by referring to the data presented in Tables 1, 2 and 3. All of the successful agents show that 2ymethyl-1-butanol and 3-methyl-1-butanol can b e separated from 1-pentanol by means of extractive distillation. and that the ease of separation is considerable.

WORKING EXAMPLE

Example 1: Fifty grams of a 2-, methyl-1-butanol, 3-, methyl-1-butanol and 1-pentanol mixture and fifty grams of 3-carene as the extractive distillation agent were charged to a vapor-liquid equilibrium still and refluxed f or two hours. The vapor composition was 70.6% 2-methyl-1-butanol-3-methyl-1-butanol, 29.4% 1-pentanol; the liquid composition was 62.3% 2-methyl-1-butanol-3-methyl-1-butanol, 37.7% 1-pentanol. This is a relative volatility of 1.45.

I claim:

1. A method for recovering 2-methyl-1-butanol and 3-methyl-1-butanol from a mixture of 2-methyl-1-butanol, 3-methyl-1-butanol and 1-pentanol which consists essentially of distilling a mixture consisting of 2-methyl-1-butanol, 3-methyl-1-butanol and 1-pentanol in the presence of an extractive distillation agent, recovering the 2-methyl-1-butanol and the 3-methyl-1-butanol as overhead product and obtaining the 1-pentanol and the extractive distillation agent as bottoms product, wherein said extractive distillation agent consists of one material selected from the group consisting of ethyl benzoate, ethyl valerate, 2-octanone, 2,6-dimethyl-4-heptanone, 2-undecanone, propiophenone, 3-methoxyacetophenone, propylene glycol phenyl ether, nitrobenzene, 2-dimethylamino-2-methyl-1-propanol, 2-nitrotoluene, 3-nitrotoluene, 1-methylpiperazine, butyrolactone, phenol, 9,6-dimethyl phenol, N,N-dimethylformamide, diethylene glycol methyl ether, 1-octene, 1,2,3,4-tetrahydronapthalene, dipentene, 3-carene, alpha-pinene, dimethylsulfoxide, tetraethyl ortho silicate, N,N-dimethyl aniline and cyclohexyl amine.

* * * * *